(12) United States Patent
Yang et al.

(10) Patent No.: US 10,460,859 B2
(45) Date of Patent: Oct. 29, 2019

(54) RESISTANCE STRUCTURE, RESISTANCE STRUCTURE UNIT, INFORMATION IDENTIFICATION DEVICE AND BIOSENSOR

(71) Applicant: VivaChek Biotech (Hangzhou) Co., Ltd., Hangzhou (CN)

(72) Inventors: Rong Yang, Hangzhou (CN); Qinggang Yang, Hangzhou (CN)

(73) Assignee: VivaChek Biotech (Hangzhou) Co., Ltd., Hangzhou (CN)

( * ) Notice: Subject to any disclaimer, the term of this patent is extended or adjusted under 35 U.S.C. 154(b) by 120 days.

(21) Appl. No.: 15/318,544

(22) PCT Filed: May 30, 2015

(86) PCT No.: PCT/CN2015/080434
§ 371 (c)(1),
(2) Date: Dec. 13, 2016

(87) PCT Pub. No.: WO2015/196900
PCT Pub. Date: Dec. 30, 2015

(65) Prior Publication Data
US 2017/0133131 A1    May 11, 2017

(30) Foreign Application Priority Data

Jun. 24, 2014  (CN) .......................... 2014 1 0287690

(51) Int. Cl.
*H01C 1/16* (2006.01)
*G01N 33/487* (2006.01)
(Continued)

(52) U.S. Cl.
CPC .............. *H01C 1/16* (2013.01); *G01N 27/26* (2013.01); *G01N 27/3271* (2013.01);
(Continued)

(58) Field of Classification Search
CPC . H01C 1/16; H01C 1/14; G01N 27/26; G01N 27/3271
(Continued)

(56) References Cited

U.S. PATENT DOCUMENTS

2005/0019953 A1    1/2005 Groll
2006/0144704 A1    7/2006 Ghesquiere et al.
(Continued)

FOREIGN PATENT DOCUMENTS

CN    102967636    *   3/2013  ............. G01N 27/26
CN    102967636 A      3/2013
(Continued)

OTHER PUBLICATIONS

European Patent Application No. 15810927.2 extended Search and Opinion dated Nov. 3, 2017, 8 pages.
(Continued)

*Primary Examiner* — Kyung S Lee
*Assistant Examiner* — Iman Malakooti
(74) *Attorney, Agent, or Firm* — Lathrop Gage LLP

(57) ABSTRACT

A resistance structure, a resistance structure unit, an information identification device and a biosensor. The resistance structure comprises: a first electrode (1); a second electrode (2); a plurality of first resistance elements (3), wherein one end of each of the first resistance elements (3) is connected to the first electrode (1), and the other end thereof is connected to the second electrode (2); a first fracture (11), the first fracture (11) dividing the first electrode (1) into a first part (111) and a second part (112), the first fracture (11) being located between two adjacent first resistance elements (3) or disconnecting at least one first resistance element (3) from the first electrode (1); and a third electrode (4), wherein the third electrode (4) is connected to the first part (111) of the first electrode (1).

37 Claims, 15 Drawing Sheets

(51) Int. Cl.
    *G01N 27/26* (2006.01)
    *H01C 1/14* (2006.01)
    *G01N 27/327* (2006.01)

(52) U.S. Cl.
    CPC ..... *G01N 33/487* (2013.01); *G01N 33/48771* (2013.01); *H01C 1/14* (2013.01)

(58) Field of Classification Search
    USPC ........................................................ 338/325
    See application file for complete search history.

(56) References Cited

U.S. PATENT DOCUMENTS

| | | | |
|---|---|---|---|
| 2010/0170791 A1 | 7/2010 | Lee | |
| 2013/0027064 A1* | 1/2013 | Austera | G01N 27/3272 324/692 |
| 2014/0124384 A1* | 5/2014 | Gerber | A61B 5/0002 205/782 |

FOREIGN PATENT DOCUMENTS

| | | |
|---|---|---|
| CN | 103733056 A | 4/2014 |
| CN | 104034767 A | 9/2014 |
| CN | 104034876 A | 9/2014 |
| CN | 104049009 A | 9/2014 |
| CN | 203965442 U | 11/2014 |
| CN | 204165979 U | 2/2015 |
| CN | 204314254 U | 5/2015 |
| WO | WO 2009076263 A1 | 6/2009 |
| WO | WO 2012064648 A1 | 5/2012 |
| WO | WO 2013143357 A1 | 10/2013 |

OTHER PUBLICATIONS

European Patent Application No. 15810927.2 Communication pursuant to Rule 114(2) EPC dated Feb. 21, 2018, 16 pages.
PCT/CN2015/080434 International Search Report and Written Opinion dated Sep. 21, 2015, 10 pages.

* cited by examiner

RESISTANCE STRUCTURE, RESISTANCE STRUCTURE UNIT, INFORMATION IDENTIFICATION DEVICE AND BIOSENSOR

CROSS REFERENCE TO RELATED APPLICATION

This application is a 35 U.S.C. § 371 national phase application of PCT/CN2015/080434, filed May 30, 2015, which application claims priority from China Patent Application No. CN 201410287690.3, filed on Jun. 24, 2014. The entire application, including all tables, diagrams and claims is incorporated hereby as reference of the present invention.

FIELD OF THE INVENTION

The present invention relates to a resistance structure, a resistance structure unit, an information identification device and a biosensor, and in particular, to a resistance structure, a resistance structure unit, an information identification device, and a biosensor used for medical examination.

DESCRIPTION OF THE RELATED ART

Biosensor technology such as biological test papers has been widely used in the field of POCT (Point of Care Test, POCT). Taking blood glucose detection technique as an example, with the advantages of operation convenience and timely detection, glucometer has been widely used as an instrument for blood glucose detection. Glucometers are roughly divided into two categories: Glucometers based on photochemical detection and those based on electrochemical detection. In photochemical test papers, blood glucose reacts with enzymes on the photochemical bio-sensing test paper of glucometer to produce chemical substances that lead to the change to the labeled substance or change to the absorption/emission wavelength, and the color change or change to absorption/emission wavelength is conveted into corresponding blood glucose concentrations. In the electrochemical test papers, when blood glucose reacts with enzymes on the electrochemical bio-sensing test paper of glucometer, with the release of electrons, the current change is converted to blood glucose concentration by the glucometer.

Since each batch of biosensors has minor difference or the same detection instrument may be used in combination with different biosensors to detect different types of analytes (eg, whole blood, urine, etc.), or the same biosensor may be used in different detection instruments, and it is required to set different calibration parameters for each batch and each type of biosensors.

In terms of blood glucose electrochemical test strips, the inter-batch differences such as differences in volume and area between the working electrode and reference electrode, amount of enzymes in the reaction zone, and different surface states of reaction electrodes, may exist in each batch, which will affect the detection results. Prior to delivery, the manufacturer will set a group of special calibration parameter values for each batch, to confirm that the test results are correct. In addition, some biosensor manufacturers may design and produce OEM test strips using the same biosensor test strips according to customers' needs, which will be used together with different detection instruments. Test strips cannot be cross-used between two kinds of detection instruments. Some manufacturers detect different analytes with only one detection instrument, therefore, before detection, the type of analytes must be judged to ensure that the test results are correct.

Currently, the calibration chips are used for setting the calibration parameters on the markets, that is, each batch of biological sensing test papers is equipped with the corresponding correction chips which store the calibration parameters. When in use, users just need to insert the calibration chips to the detection instrument, and then use the matching batch of test papers to obtain the accurate test results. However, users often forget this step in actual detection, leading to inaccurate test results.

In order to solve this problem, US patent application US20100170791A1 discloses an electrode design in which different resistance ratios between a plurality of contacts of the electrode may be assigned different identification information, in other words, different correction parameters may be provided. Users can connect the detection instrument to any two contacts of the electrode to obtain different calibration parameters, and enter them to the detection instrument for calibration. However, this invention requires pre-storage of a large number of calibration parameters, and a large number of contacts must be designed on the biosensor and the detection instruments also need addition of contacts, leading to increased product cost.

SUMMARY OF THE INVENTION

One object of the present invention is to provide a novel resistance structure which can be used in an information identification device and a biosensor. Another object of the invention is to provide an n information identification device and a biosensor that use the above novel resistance structure.

Other objects, features and d advantages of the present invention will become apparent from the following detailed description, or may be partially understood through practices of the invention.

According to some embodiments herein, a resistance structure includes: a first electrode; a second electrode; a plurality of first resistance elements, wherein one end of each of the first resistance elements is connected to the first electrode, and the other end thereof is connected to the second electrode; a first fracture, the first fracture dividing the first electrode into a first part and a second part, the first fracture being located between two adjacent first resistance elements or disconnecting at least one first resistance element from the first electrode; a third electrode, wherein the third electrode is connected to the first part of the first electrode. a first contact, connecting with the second part of the first electrode; a second contact, connecting with the second electrode; and a third contact, connecting with the third electrode.

According to some embodiments herein, the second part of the first electrode further has N second fractures, N being a natural number greater than 0, each of the N second fractures being located between two adjacent first resistance elements or disconnecting at least one first resistance element from the first electrode, the N second fractures divide the first part into (N+1) parts, the third electrode is connected with one of the (N+1) parts.

According to some embodiments herein, the resistances of the plurality of first resistance elements are the same each other.

According to some embodiments herein, the resistances of at least part of the plurality of first resistance elements are different.

According to some embodiments herein, the material of the first electrode and the second electrode is different from that of the first resistance element.

According to some embodiments herein, both the resistance of the first electrode and the second electrode is less than that of each first resistance element.

According to some embodiments herein, the second electrode further has M third fractures, M being a natural number greater than 0, each of the M third fractures being located between two adjacent first resistance elements or disconnecting at least one first resistance element from the second electrode.

According to some embodiments herein, a resistance structure includes: a first resistance structure; a second resistance structure; a first contact, connected to the first resistance structure;

a second contact, connected to the second resistance structure; a third contact, connected to the first resistance structure; a fourth contact, connected to the second resistance structure, wherein the first resistance structure includes: a first electrode; a second electrode; a plurality of first resistance elements, wherein one end of each of the first resistance elements is connected to the first electrode, and the other end thereof is connected to the second electrode; at least one fractures, dividing the first electrode into at least two parts, each of the fractures is located between two adjacent first resistance elements or disconnecting at least one first resistance elements from the first electrode, wherein, a first electrical parameter R1 is provided between the first contact and the third contact, and a second electrical parameter R2 is provided between the second contact and the fourth contact, the first electrical parameter R1 varies with the location of at least one of the fractures.

According to some embodiments herein, an information identification device, including the resistance structure unit as claimed in any one of aforesaid claims.

According to the first aspect of the invention, a resistance structure includes: a first electrode;

a second electrode; a plurality of first resistance elements, wherein one end of each of the first resistance elements is connected to the first electrode, and the other end thereof is connected to the second electrode; a first fracture, the first fracture dividing the first electrode into a first part and a second part, the first fracture being located between two adjacent first resistance elements or disconnecting at least one first resistance element from the first electrode; a third electrode, wherein the third electrode is connected to the first part of the first electrode; a first contact, connecting with the second part of the first electrode; a second contact, connecting with the second electrode; and a third contact, connecting with the third electrode.

According to the first aspect of the invention, on the basis of the first aspect, the second part of the first electrode further has N second fractures, N being a natural number greater than 0, each of the N second fractures being located between two adjacent first resistance elements or disconnecting at least one first resistance element from the first electrode, the N second fractures divide the first part into (N+1) parts, the third electrode is connected with one of the (N+1) parts.

According to the seventh aspect of the invention, on the basis of the first or second aspect, the second electrode further has M third fractures, M being a natural number greater than 0, each of the M third fractures being located between two adjacent first resistance elements or disconnecting at least one first resistance element from the second electrode.

According to the sixteenth aspect of the invention, a resistance structure unit includes the resistance structures as described in any one of first to fifteenth aspects.

According to the seventeenth aspect of the invention, a resistance structure includes: a first electrode; a second electrode; a plurality of first resistance elements, wherein one end of each of the first resistance elements is connected to the first electrode, and the other end thereof is connected to the second electrode; N fractures, the N fractures dividing the first electrode into N+1 parts, each of the N fractures is located between two adjacent first resistance elements or disconnecting at least one first resistance element from the first electrode, N is a natural number greater than 1; a first contact; a second contact; and a third contact, each of the first contact, the second contact and the third contact is connected to or connected via a resistance structure to one of the N+1 parts, the resistance structure includes at least one resistance elements.

According to the eighteenth aspect of the invention, a resistance structure includes: a first electrode; a second electrode; a plurality of first resistance elements, wherein one end of each of the first resistance elements is connected to the first electrode, and the other end thereof is connected to the second electrode; N fractures, the N fractures dividing the first electrode into N+1 parts, each of the N fractures is located between two adjacent first resistance elements or disconnecting at least one first resistance element from the first electrode, N is a natural number greater than 0; a third electrode; a fourth electrode; a first sub-resistance structure, including at least one resistor, where the first sub-resistance structure connects the third electrode to at least one of the (N+1) parts of the first electrode; a second sub-resistance structure, including at least one resistor, where the second sub-resistance structure connects the fourth electrode to at least part of the second electrode; a first contact, connecting one of the (N+1) parts of the first electrode;

a second contact, connecting one of the second contact and the fourth electrode; and a third contact, connecting with the third electrode.

According to the nineteenth aspect of the invention, a resistance structure includes: a first electrode; a second electrode; a plurality of first resistance elements, wherein one end of each of the first resistance elements is connected to the first electrode, and the other end thereof is connected to the second electrode; N fractures, the N fractures dividing the first electrode into N+1 parts, each of the N fractures is located between two adjacent first resistance elements or disconnecting at least one first resistance element from the first electrode, N is a natural number greater than 0; a third electrode; a fourth electrode; a first sub-resistance structure, including at least one resistor, where the first sub-resistance structure connects the third electrode to at least part of the second electrode or one of the (N+1) parts; a second sub-resistance structure, including at least one resistor, where the second sub-resistance structure connects the fourth electrode to the third electrode or at least part of the second electrode or one of the (N+1) parts;

a first contact, connected to or connected via a third sub-resistance structure to one of the (N+1) parts of the first electrode, the second sub-resistance structure at least includes a resistance element; a second contact; and a third contact, wherein, each of the second contact and the third contact is connected to one of the second electrode, the third electrode and the fourth electrode.

According to the twentieth aspect of the invention, a resistance structure includes: a first electrode; a second electrode; a plurality of first resistance elements, wherein one end of each of the first resistance elements is connected to the first electrode, and the other end thereof is connected to the second electrode; N fractures, the N fractures dividing the first electrode into N+1 parts, each of the N fractures is located between two adjacent first resistance elements or disconnecting at least one first resistance element from the first electrode, N is a natural number greater than 0; a third electrode; a first sub-resistance structure, including at least one resistor, where the first sub-resistance structure connects the third electrode to at least part of the second electrode; a first contact; a second contact; and a third contact, each of the first contact and the second contact is connected to or connected via a second sub-resistance structure to one of the (N+1) parts, the second sub-resistance structure includes at least one resistance element, the third contact is connected with the third electrode.

According to the twenty-first aspect of the invention, a resistance structure includes: a first resistance structure; a second resistance structure; a first contact, connected to the first resistance structure; a second contact, connected to the second resistance structure; a third contact, connected to the first resistance structure; a fourth contact, connected to the second resistance structure, wherein the first resistance structure includes: a first electrode; a second electrode; a plurality of first resistance elements, wherein one end of each of the first resistance elements is connected to the first electrode, and the other end thereof is connected to the second electrode; at least one fractures, dividing the first electrode into at least two parts, each of the fractures is located between two adjacent first resistance elements or disconnecting at least one first resistance elements from the first electrode, wherein, a first electrical parameter R1 is provided between the first contact and the third contact, and a second electrical parameter R2 is provided between the second contact and the fourth contact, the first electrical parameter R1 varies with the location of at least one of the fractures.

According the twenty-second aspect of the invention, on the basis of the twenty-first aspect herein, the second resistance structure includes at least a portion of the first resistance structure.

According the twenty-third aspect of the invention, on the basis of the twenty-second aspect herein, one of the second contact and the fourth contact is a common contact common to one of the first contact and the third contact.

According the twenty-fourth aspect of the invention, on the basis of the twenty-third aspect herein, the second electrical parameter R2 varies with the location of at least one of the fractures.

According the twenty-fifth aspect of the invention, on the basis of the twenty-first aspect herein, the second resistance structure including: a third electrode; a fifth electrode; a plurality of second resistance elements, wherein one end of each of the second resistance elements is connected to the third electrode, and the other end thereof is connected to the fifth electrode; wherein at least one of the third electrode and the fifth electrode has at least one second fracture such that the third electrode or the fifth electrode is divided into at least two parts, at least one of the second fractures is located between two adjacent first resistance elements or disconnecting at least one first resistance elements from the third electrode or the fifth electrode.

According to the thirty-second aspect of the invention, on the basis of the twenty-sixth aspect herein, the second electrode further has M third fractures, M being a natural number greater than 0, each of the M third fractures being located between two adjacent first resistance elements or disconnecting at least one first resistance element from the second electrode.

According to the thirty-ninth aspect of the invention, an information identification device, including the resistance structure unit as described in any one of the $16^{th}$, $26^{th}$-$38^{th}$ aspects.

According to the fortieth aspect of the invention, on the basis of the thirty-ninth aspect herein, the information identification device is used to identify the identification information through the ratio of an electrical parameter characterized by the resistance structure to a second electrical parameter.

According to the forty-second aspect of the invention, on the basis of the thirty-ninth aspect herein, the second electrical parameters are dependent or independent of the resistance structure.

According to the forty-third aspect of the invention, on the basis of the thirty-ninth aspect herein, the second electrical parameters are from a test instrument.

According to the forty-fourth aspect of the invention, a biosensor, including: a biosensor body, including a working electrode and a counter electrode disposed on an insulating base plate; and an information identification device as described in any one of the 39th-43rd aspects, disposed on the insulating base plate.

According to the forty-fifth aspect of the invention, on the basis of the forty-fourth aspect, the information identification device and the working electrode and the counter electrode are located on the same surface of the insulating base plate, and the information identification device is electrically isolated from the working electrode and the counter electrode or connected to one of the working electrode and the counter electrode.

According to the forty-sixth aspect of the invention, on the basis of the forty-fourth aspect, the information identification device and the working electrode and the counter electrode are located on different surfaces of the insulating base plate.

According to the forty-seventh aspect of the invention, on the basis of the forty-fourth aspect, the first electrode, the second electrode, and the plurality of first resistance elements are formed by a printing mode.

The resistance structure, resistance structure unit, identification information unit, information identification device and biosensor disclosed herein are simple in structure, rich in formation, which can reduce the cost and lower the processing complexity.

DETAILED DESCRIPTION

Figure 1:
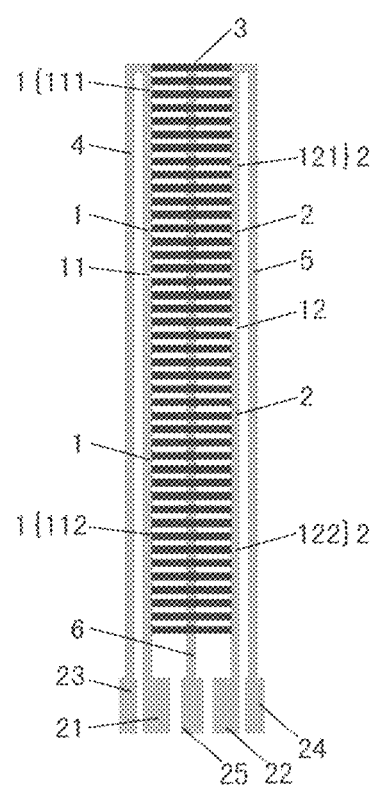
FIG. 1 is a schematic diagram of a resistance structure according to an embodiment of the invention.

The invention will be described comprehensively in combination with drawings and embodiments. However, the embodiments can be implemented in a variety of ways but should not be construed as limited to the embodiments set forth herein; on the contrary, these embodiments are provided so that the invention will be disclosed comprehensively and completely, and the concept of the embodiments will be conveyed to those skilled in the art. In the figures, the thickness of region and layer is exaggerated for the purpose of clarity; the same reference numerals denote the same or similar parts, so the repeated description thereof can be omitted.

Furthermore, the features, structures, or characteristics described herein may be combined in one or more embodiments in any appropriate mode. In the following, numerous specific details are set forth in order to provide a thorough understanding of embodiments of the present invention. However, those skilled in the art should be aware that the technical solutions in the invention may be practiced without one or more of the specific details or other methods, components and materials can be used, etc. In other circumstances, well-known structures, materials, or operations are not shown or described in detail to avoid obscuring aspects of the invention.

Exemplary embodiments embodying the features and advantages of the present invention will be described in details below. It should be understood that various modifications in the various embodiments to the invention will not be departed from the scope of the invention, and descriptions and drawings herein are intended to be illustrative rather than a limitation of the invention.

The present invention discloses a resistance structure, a unit or device including the resistance structure and a biosensor, which can generate different codes for the use of detection instrument according to different fracture positions corresponding to different electrical parameters. In the following, different embodiment will be described as examples.

Example 1

Figure 14:
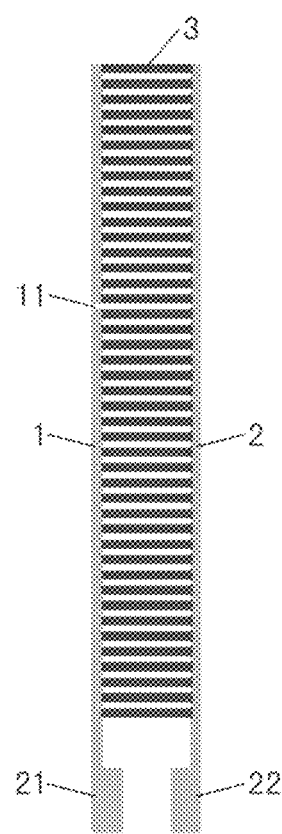
FIG. 14 is a schematic diagram of a resistance structure according to an embodiment of the invention.

FIG. 14 shows the resistance structure shown in the first embodiment of the present invention. As shown in FIG. 14, the resistance structure includes a first electrode 1, a second electrode 2, and a plurality of first resistance elements 3. A plurality of first resistance elements 3 are connected between the first electrode 1 and the second electrode 2. The resistance structure further includes a first contact 21 connected to first electrode 1 and a second contact 22 connected to second electrode 2. The first electrode 1 has a first fracture 11, first fracture 11 being located between two adjacent first resistance elements 3 and dividing first electrode 1 into a first part 111 and a second part, but the present invention is not limited thereto; first contact 21 is connected to the second part, and a first electrical parameter R1 is provided between first contact 21 and second contact 22. The first electrical parameter R1 may be, for example, a resistance value. However, the present invention is not limited thereto. For example, the first electrical parameter R1 can also be impedance, voltage, or current value obtained when the external measurement system is connected to first contact 21 and second contact 22. The electrical parameters discussed below are similar. It should be noted that, in the present embodiment and following embodiment, the first part 111 refers to a portion located on the upper side of the drawing, and second part 112 refers to a portion located on the lower side of the drawing.

In the present embodiment, as shown in FIG. 14, when the detection device is connected to first contact 21 and second contact 22, the first electrical parameter R1 is detected, and the first electrical parameter R1 varies with the position of the first fracture 11. For example, in the present embodiment, the first electrical parameter R1 is the resistance value, and when the position of the first fracture 11 changes, the value of the resistance in the electrical circuit composed of the first electrode 1, a plurality of first resistance element 3 and second electrode 2 connected in parallel below the first fracture 11 will vary with the number of first resistance elements 3 connected in parallel, therefore, the different location of the first fracture 11 will result in difference in first electrical parameter R1.

However, the aforesaid first electrical parameter R1 may be not limited to a resistance value, but may also be other electrical parameters such as a current value, a voltage value, etc., which is not limited in the invention.

Referring to FIG. 14, in this embodiment, first electrode 1 and second electrode 2 are electrodes arranged in parallel with each other, and a plurality of first resistance elements 3 are electrodes arranged in parallel between first electrode 1 and second electrode 2, but it is not limited thereto in the invention. It should be easily understood that, first electrode 1 and second electrode 2 may not parallel to each other. First electrode 1 and second electrode 2 are longitudinal electrodes, and first resistance elements 3 are a plurality of lateral electrodes. The plurality of first resistance elements 3 may be the same as each other or may be different from each other. In this embodiment, the electrodes are the same, namely, each of first resistance elements 3 has the same material, size, resistivity, etc.

After the detection instrument detects the first electrical parameter R1, the corresponding codes can be calculated according to the formula stored in the detection instrument, or codes can be directly obtained according to the first electrical parameter R1. Different codes correspond to different information, for example, corresponding to different batches of test papers, and test papers for detection of different types of samples, etc., thus the detection instrument provides different calibration parameters to make the test results more accurate.

Example 2

Figure 6:
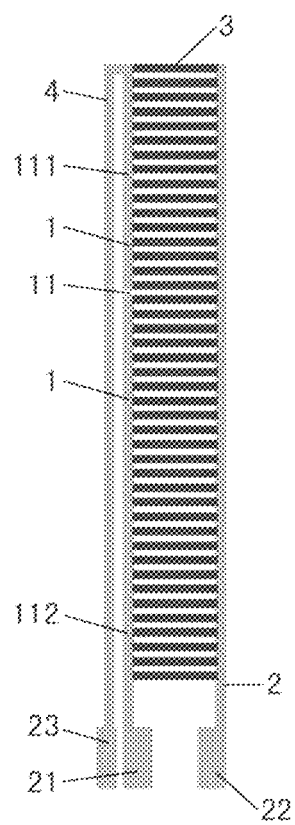
FIG. 6 is a schematic diagram of a resistance structure according to an embodiment of the invention.

FIG. 6 is a second embodiment of the resistance structure of the present invention. In the present embodiment, the resistance structure has a third electrode 4 and a third contact 23 as compared with the first embodiment shown in FIG. 14. The third electrode 4 is connected to a first part 111 of a first electrode 1, and a third contact 23 is connected to a third electrode 4. The first contact 21, second contact 22 and third contact 23 can be connected to the detector.

When the electrodes of the detection instrument are connected to first contact 21 and second contact 22, a first electrical parameter R1 is provided between first electrode 1, a plurality of first resistance elements 3 connected in parallel located below the first fracture 11 and second electrode 2;

When the electrodes of the detection instrument are connected to second electrode 22 and third contact 23, a second electrical parameter R2 is provided between second electrode 2, a plurality of first resistance elements 3 connected in parallel located above the first fracture 11 and third electrode 4;

The values of R1 and R2 will vary with the position of fracture 11 on the first electrode 1, and will therefore change accordingly.

The number of first resistance elements is a natural number, and at least two, the resistance value can be changed by changing the area, width, material of each or part of first resistance elements, to change R1, R2 values, for example, as shown in FIG. 8A-8D.

The different material and/or different conductive area of first resistance element 3 leads to different conductive parameters, wherein, if the first fracture 11 remains the same, the two first resistance elements 3 are machined to electrodes of two different conductive materials, or electrodes of the same material but different in area, so as to change the values of R1 and R2, for example, as shown in FIG. 9A-9E.

Example 3

Figure 15:
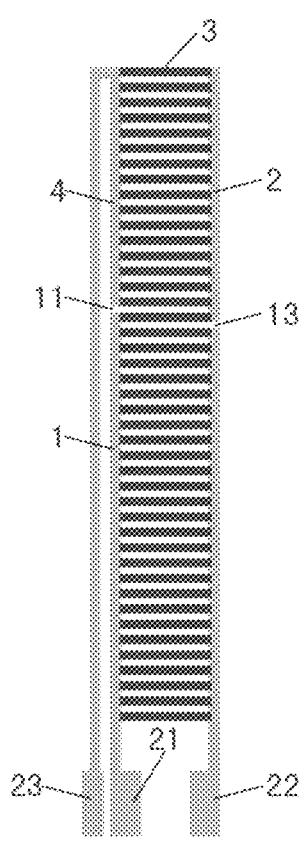
FIG. 15 is a schematic diagram of a resistance structure according to an embodiment of the invention.

FIG. 15 shows the resistance structure as shown in the third embodiment of the present invention. Referring to FIG. 15, in the present embodiment, second electrode 13 is further provided with third fracture 13 as compared with the second embodiment. The third fracture 13 is located between two adjacent first resistance elements 3 and divides second electrode 2 into a first part 121 and a second part 122, and the second contact 22 is connected to the first part 121 of the second electrode 2.

In the present embodiment, the second electrical parameter R2 varies with the locations of the first fracture 11 and the third fracture 13, wherein the number of first resistance elements connected to the upper part 111 of the first fracture 11 is not equal to the number of first resistance elements connected to the upper part 131 of the third fracture 13.

After the detection instrument detects the first electrical parameter R1 between the first contact 21 and the second contact 22 and the second electrical parameter R2 between the third contact and the second contact, the corresponding codes can be calculated according to the formula stored in the detection instrument. Different codes correspond to different information, for example, test papers corresponding to different batches, and test papers for detection of different types of samples, etc., thus the detection instrument provides different calibration parameters to make the test results more accurate.

Example 4

Figure 16:
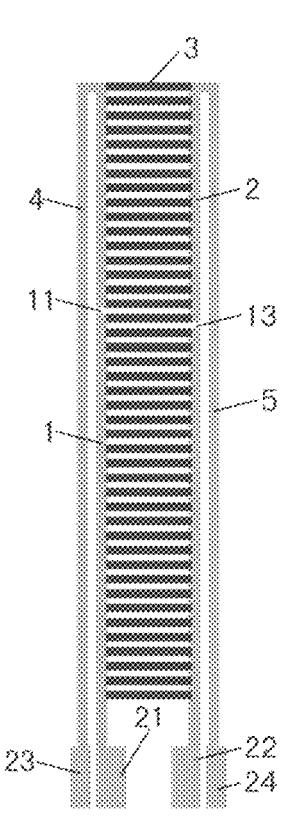
FIG. 16 is a schematic diagram of a resistance structure according to an embodiment of the invention.

FIG. 16 shows the resistance structure shown in the fourth embodiment of the present invention. Referring to FIG. 16, in the present embodiment, the resistance structure further includes the fourth electrode 5 and the fourth contact 24; the fourth electrode 5 is connected with the first part 121 of the second electrode 2, and the fourth contact 24 is connected with the fourth electrode 5. In this embodiment, in addition to the first electrical parameter R1 between first contact 21 and second contact 22, and second electrical parameters R 2 between first contact 21 and third contact 23, there may be other electrical parameters between first contact 21 and fourth contact 24. These electrical parameters can be varied with the location of fractures, so that more codes can be extended by different combinations of electrical parameters, to correspond to different information.

Example 5

Figures 7A, 7B:
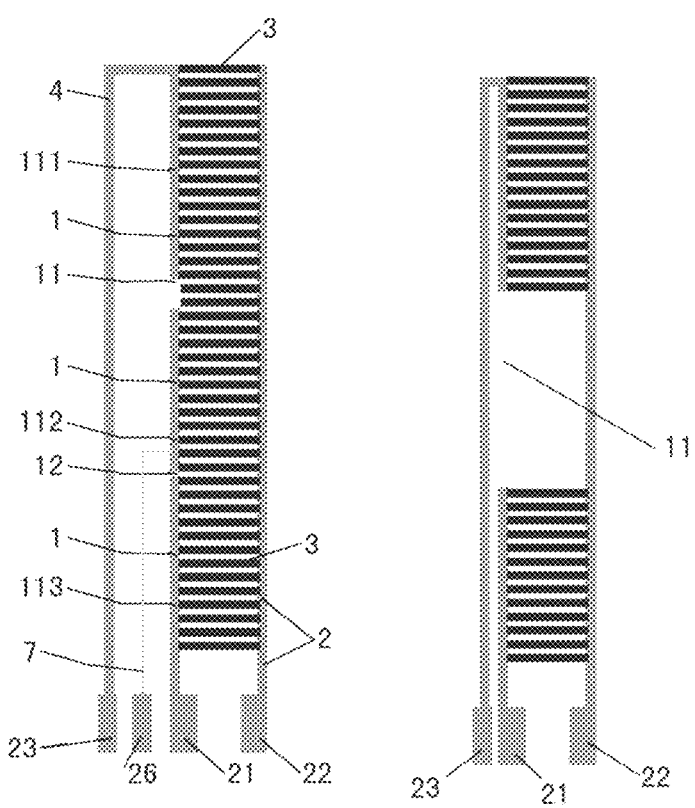
FIG. 7A and FIG. 7B are schematic diagrams of a resistance structure according to an embodiment of the invention.
Figures 8A, 8B:
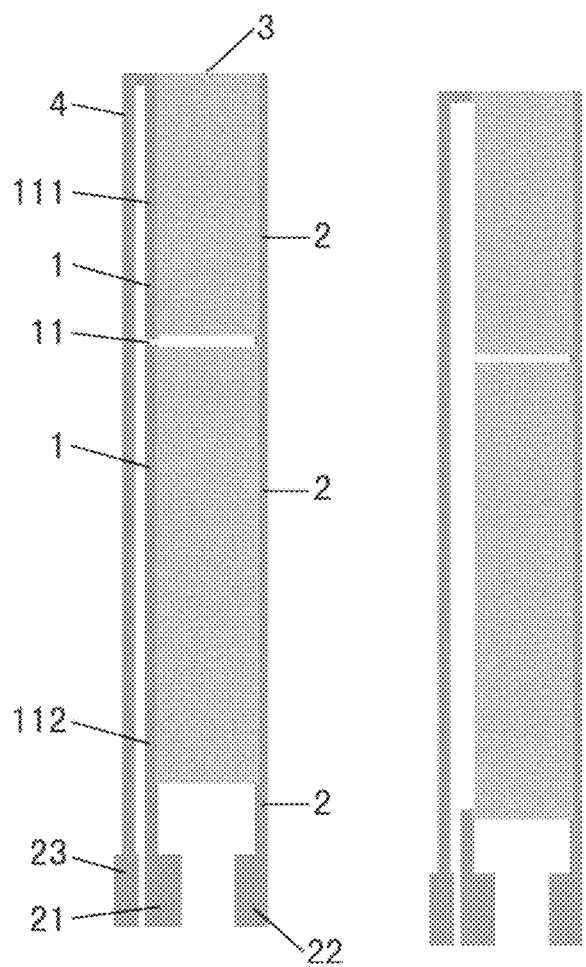
FIG. 8A to FIG. 8D are schematic diagrams of a resistance structure according to an embodiment of the invention.
Figures 8C, 8D:
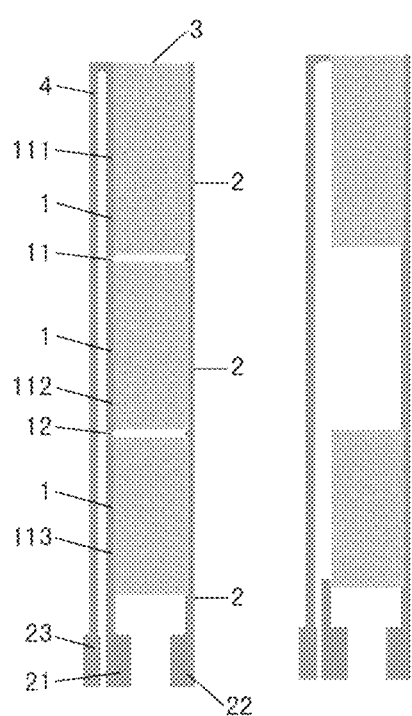

FIGS. 7A and 7B are schematic views of a fifth embodiment of a resistance structure in the invention. In this embodiment, as shown in FIG. 7A, the first electrode 1 has a second fracture 12 in addition to a first fracture 11, as compared with the resistance structure shown in the second embodiment in FIG. 6. The first fracture 11 and second fracture 12 divide the first electrode 1 into a first part 111 located above and a second part 113 located below, and a third part 112 located in the middle. In addition, the third part may be connected to the sixth electrode 7, and one end of which may be connected to the sixth contact 26.

Referring to FIG. 7A, a resistance structure may be provided for an information identification device or other device. The resistance structure can be configured, including: a first electrode 1; a second electrode 2; a plurality of first resistance elements 3, one end of each of the first resistance elements 3 is connected to the first electrode 1, and the other end thereof is connected to the second electrode 2; N fractures 11 and 12, the N fractures 11 and 12 dividing the first electrode into (N+1) parts 111, 112 and 113, each of N fractures 11 and 12 being located between two adjacent first resistance elements 3 or disconnecting at least one first resistance element 3 from the first electrode 1, N being a natural number greater than 1; a first contact 21, a sixth contact 26, and a third contact 23.

Each of the first contact 21, the sixth contact 26, and the third contact 23 are connected to one of the (N+1) parts 111, 112 and 113. According to some embodiments, at least one of the first contact 21, second contact 26 or third contact 23 may also be connected to one of the (N+1) parts 111, 112 and 113. The resistance structure may include at least one resistance element. The resistance structure is not shown in FIG. 7A, but reference can be made to FIGS. 21-23.

Example 6

Figure 17:
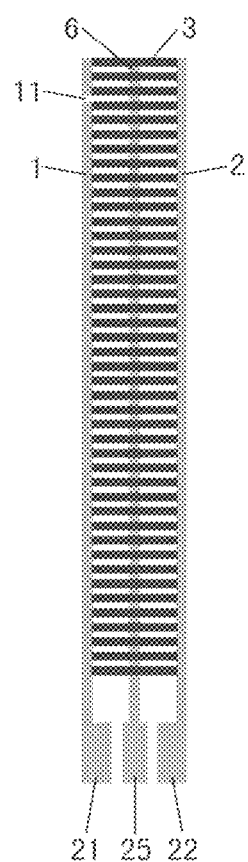
FIG. 17 is a schematic diagram of a resistance structure according to an embodiment of the invention.
Figure 18:
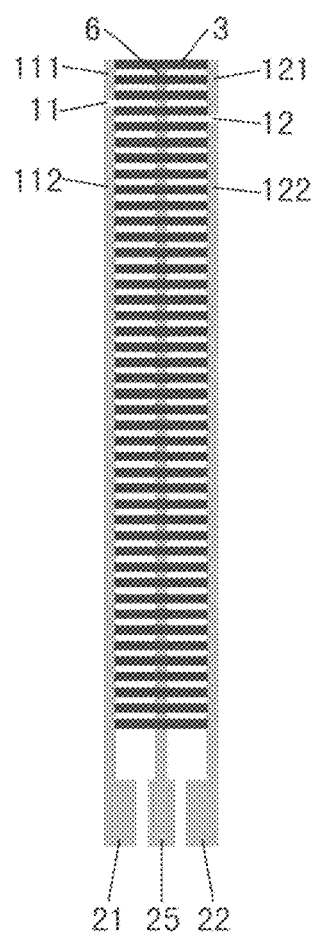
FIG. 18 is a schematic diagram of a resistance structure according to an embodiment of the invention.

FIGS. 17-18 show the electrical structure as shown in the sixth embodiment. Referring to FIG. 7, compared with the first embodiment, the resistance structure in this embodiment further includes a fifth electrode 6 and a fifth contact 25, the fifth electrode 6 is connected each other and passes through each of the first resistance elements 3. The fifth contact 25 is connected with the fifth electrode 6.

The first electrode 1 has the first fracture 11, which is located between two adjacent first resistance elements 3 and divides first electrode 1 into first part 111 and second part 112. First contact 21 is connected with second part 112 of first electrode 1. As shown in FIG. 18, the second electrode 2 has a second fracture 12, which is located between two adjacent first resistance elements 3. There is at least one fractures in first fracture 11 and second fracture 12.

Electrical parameter R1 can be provided between first contact 21 and fifth contact 25, and electrical parameter R3 can be provided between second contact 22 and fifth contact 25.

S=K*R1/R3, where, the electrical parameters of R1 or R3 may vary with the fracture position, and more codes can be extended by different combinations of electrical parameters to correspond to different information.

Example 7

Figure 19:
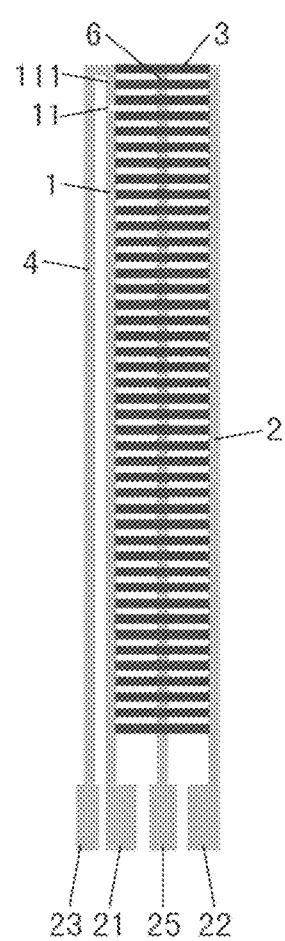
FIG. 19 is a schematic diagram of a resistance structure according to an embodiment of the invention.
Figure 20:
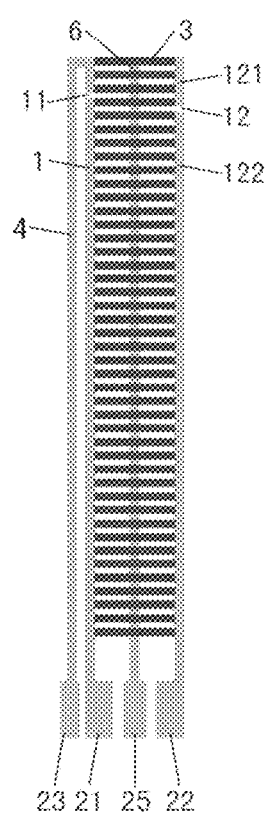
FIG. 20 is a schematic diagram of a resistance structure according to an embodiment of the invention.

FIGS. 19-20 are the electrical structures shown in the seventh embodiment of the present invention. As shown in FIG. 19, the resistance structure in this embodiment further includes third electrode 4 and third contact 23 as compared with the sixth embodiment. Third electrode 4 is connected with first part 111 of first electrode 1, and third contact 23 is connected with third electrode 4. Of which, electrical parameter R1 is provided between first contact 21 and fifth contact 25, electrical parameter R2 is provided between third contact 23 and fifth contact 25, and electrical parameter R3 can be provided between second contact 22 and fifth contact 25. In the present embodiment, these electrical parameters vary with the fracture position, and more codes can be extended by different combinations of electrical parameters to correspond to different information.

Example 8

Figure 2:
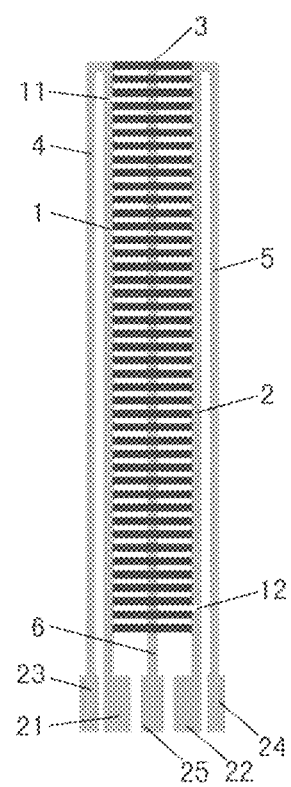
FIG. 2 is a schematic diagram of a resistance structure according to an embodiment of the invention.
Figure 3:
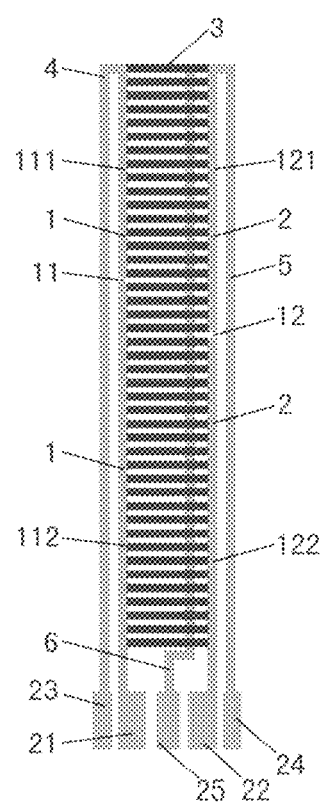
FIG. 3 is a schematic diagram of a resistance structure according to an embodiment of the invention.
Figure 4:
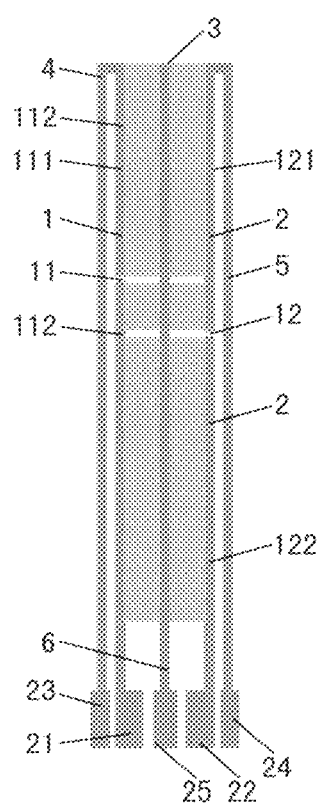
FIG. 4 is a schematic diagram of a resistance structure according to an embodiment of the invention.
Figure 5:
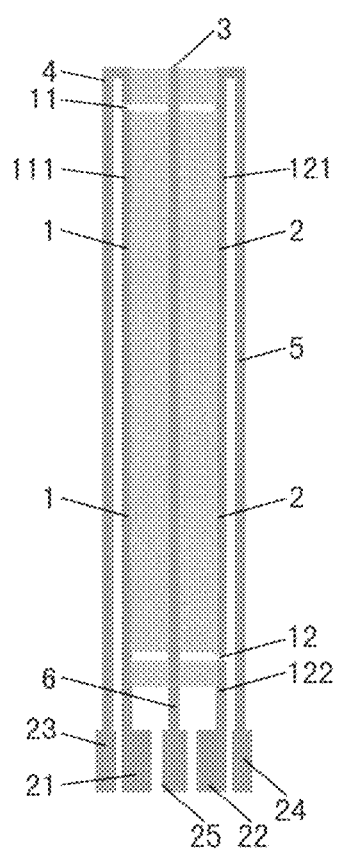
FIG. 5 is a schematic diagram of a resistance structure according to an embodiment of the invention.

FIGS. 1 to 3 show the eighth embodiment of the present invention, showing a schematic view of the resistance structure. Referring to FIG. 1, the resistance structure in this embodiment further includes the fourth electrode 5 and the fourth contact 24 as compared with the seventh embodiment. The fourth electrode 5 is connected to first part 121 of second electrode 2, and fourth contact 24 is connected to fourth electrode 5. Electrical parameter R4 is provided between fourth contact 24 and fifth contact 25. The first electrical parameter R1, second electrical parameter R2, third electrical parameter R3 and fourth electrical parameter R4 vary with the positions of first fracture 11 and second fracture 12, so that more codes can be extended by combinations of different electrical parameters to correspond to different information.

In this embodiment, a plurality of first resistance elements 3 are arranged in parallel and the same as each other, and the fifth electrode 6 passes through the middle point of the first resistance element 3 in the length direction, namely, each first resistance element 3 can be divided into two parts of equal length. In practices, the two parts may be of unequal length.

The first electrode 1, the second electrode 2, the third electrode 4, the fourth electrode 5 and the fifth electrode 6 are connected to the detection instrument through the first contact 21, the second contact 22, the third contact 23, the fourth contact 24, and the fifth contact 25. The electrodes of the detection instrument are connected to different contacts, to obtain corresponding correction information parameters, which is described in details below.

R1-R4 may vary with the positions of first fracture 11 and second fracture 12, and more codes can be extended by different combinations of electrical parameters to correspond to different information.

When the position of fracture is unchanged, the fifth electrode is not in the midpoint of the first resistance element, which causes different resistance of the left and right parts of the first resistance element. The electrical parameter Rn may also be changed, thereby changing the Sn value.

Example of Information Identification Device

The present invention provides an information identification device, including an insulating base plate and a resistance structure disposed on an insulating base plate. Of which, the resistance structure may be the one as mentioned in above embodiment. It will be described in combination with embodiments below.

The First Embodiment of the Information Identification Device

In the first embodiment of the information identification device, taking the embodiment of FIG. 1 is taken as an example, as shown from FIG. 1, first electrical parameter R1 is provided between third contact 23 and fifth contact 25, electrical parameter R2 is provided between first contact 21 and fifth contact 25, and electrical parameter R3 can be provided between second contact 22 and fifth contact 25, and electrical parameter R4 is provided between fourth contact 24 and fifth contact 25, when the information identification device of the eighth embodiment of the present invention is connected with the detection instrument via electrodes and contacts, the detection instrument measures the resistance values of the electrode circuit as Rn and Rn, and the resistance ratio Sn is obtained by the equation as follows:

$$Sn = Kn * \frac{Ra}{Rb}$$

Where n=1-4, Sn is the resistance ratio, Kn is the correction coefficient, and the correction coefficient is obtained by many tests to make the actual value approximate to theoretical value in the actual process. Ra and Rb represent any two values of R1-R4, a=1-4, b=1-4, a≠b, with a total of 12 combinations, as follows:

$$S1 = K1 * \frac{R1}{R2}$$

$$S2 = K2 * \frac{R3}{R4}$$

$$S3 = K3 * \frac{R1}{R3}$$

$$S4 = K4 * \frac{R1}{R4}$$

$$S5 = K5 * \frac{R2}{R1}$$

$$S6 = K6 * \frac{R2}{R3}$$

$$S7 = K7 * \frac{R2}{R4}$$

$$S8 = K8 * \frac{R3}{R1}$$

$$S9 = K9 * \frac{R3}{R2}$$

$$S10 = K10 * \frac{R4}{R1}$$

$$S11 = K11 * \frac{R4}{R2}$$

$$S12 = K12 * \frac{R4}{R3}$$

Where, K1, K2, . . . , K12 are the correction coefficients, respectively.

In actual applications, a S value or a combination of multiple S values can be selected for identification of information as required, for example, the detection instrument can select corresponding technical parameters according to different S1 value, or select corresponding technical parameters according to the combination of S1 and S2 values. In general, when calculated according to the above formula, two groups of S1, S2 that are not associated in the circuit are selected as the best and simplest way.

According to different biosensor production batches, different calibration parameter calibration equations, and instrument models or different analytes to be determined, the electrodes of detection instrument can be connected to different contacts, thereby the information identification device gives different resistance ratio S1 to S12. The detection instrument selects appropriate technical parameters based on different information of S1-S12 and the combinations thereof, finally the detection results are obtained or which type of analyte detection is carried out.

In addition, the present invention is not limited to above examples. For example, an electrical parameter is provided between any two contacts from first contact 21 to fifth contact 25, and any two encoded parameters applicable to the above formula can be selected for encoding.

Referring to FIG. 2, when the positions of the first fracture 11 and/or the second fracture 12 are changed, the Ra and Rb are changed so that the respective Sns are changed, and thereby the recognition information given by Sn is also changed accordingly.

Referring to FIG. 1 and FIG. 2, in this eighth embodiment, the resistance value of each first resistance element 3 is substantially the same, e.g. R', and the resistances of the first electrode 1, the second electrode 2, the third electrode 4, the fourth electrode 5 and the fifth electrode 6 can be ignored, then $$S1 = K1 * \frac{R1}{R2} = K1 * \frac{\left(\frac{1}{R'}\right) * x_1}{\frac{1}{\left(\frac{1}{R'}\right)} * x_2} = K1 * \frac{x_2}{x_1}$$

Where, x1 is the number of circuits between the third contact 23 and the fifth contact 25 that pass through the first resistance element 3; x2 is the number of circuits between the first contact 21 and the fifth contact 25 that pass through the first resistance element 3. Similarly, $$S2 = K2 * \frac{R3}{R4} = K2 * \frac{\left(\frac{1}{R'}\right) * x_3}{\frac{1}{\left(\frac{1}{R'}\right)} * x_4} = K2 * \frac{x_4}{x_3}$$

Where, x3 is the number of circuits between the second contact 22 the fifth contact 25 that pass through the first resistance element 3; x4 is the number of circuits between the fourth contact 24 and the fifth contact 25 that pass through the first resistance element 3.

Therefore, when the resistance of each first resistance element 3 is substantially the same, the ratio of the resistance values between different circuits is equal to the reciprocal of the number of the first resistance elements 3 connected in parallel in the circuit. Of course, the invention is not limited thereto. When the ratio cannot be obtained by the number of resistance elements, the ratio can be available from the resistance values by calculation or simulation.

S value can be set to a value within a range of error, for example, when the range of error is $$\pm \frac{1}{2x'},$$

the same group of technical parameters are used for detection and calculation of results within the range of $$S \pm \frac{1}{2x' \mid}.$$

The Second Embodiment of the Information Identification Device

As shown in FIG. 3, when first resistance element 3 is divided into two sections with unequal length by the fifth electrode 6, the S value in the eighth embodiment also changes, so as to achieve the purpose of information identification.

For example, when the first resistance element 3 is divided by the fifth electrode 6 into two sections with length ratio of 3:1 and the resistance of 1 unit is n, then the actual resistance is 3n:n and the S3 can be calculated according to the following way:

$$S3 = K3 * \frac{R1}{R3} = K3 * \frac{\left(\frac{1}{3n}\right) * x_1}{\frac{1}{\left(\frac{1}{n}\right) * x_3}} = K3 * \frac{3x_3}{x_1}$$

The Third Embodiment of the Information Identification Device

Referring to FIG. 6, when the information identification device is electrically connected with the detection instrument via electrodes and contacts, the detection instrument calculates S1 according to R1 and R2, and selects appropriate technical parameters based on information of different S1 values, finally the detection results are obtained or which type of analyte detection is carried out. Of which, S1 can be calculated according to the following formula:

$$S1 = K1 * \frac{R1}{R2} = K1 * \frac{\frac{1}{R' * x_1}}{\frac{1}{R' * x_2}} = K1 * \frac{x_2}{x_1}$$

The Fourth Embodiment of the Information Identification Device

Referring to FIG. 7A and FIG. 7B, with the increase in fracture, R1 and R2 will vary with the position of the first fracture 11, second fracture 12 on the electrode, thus, S1=K1*R1/R2 will also change accordingly. When the contact of the resistance structure described in FIG. 7 is electrically connected with the detection instrument, the detection instrument selects appropriate technical parameters based on information of different S1 values, finally the detection results are obtained or which type of analyte detection is carried out. Alternatively, the resistance structure in the present embodiment may be further simplified as shown in FIG. 7B, that is, a plurality of first resistance element 3, the sixth electrode 7, and the sixth contact 26 that are connected to the third part of first electrode 1 are omitted compared with FIG. 7A. Users can connect the detection instrument with first contact 21 and second contact 22 or with second contact 22 and third contact 23 to detect R1 and R2. The detection instrument calculates S1 according to R1 and R2, and selects appropriate technical parameters based on information of different S1 values, finally the detection results are obtained or which type of analyte detection is carried out. Of which, S1 can be calculated according to the following formula:

$$S1 = K1 * \frac{R1}{R2} = K1 * \frac{\frac{1}{R' * x_1}}{\frac{1}{R' * x_2}} = K1 * \frac{x_2}{x_1}$$

The Fifth Embodiment of the Information Identification Device

Referring to FIGS. 8A to 8D, R1 and R2 will vary with the position of the first fracture 11, second fracture 12 on the electrode, thus, S1 will also change accordingly. When the information identification device in FIGS. 8A to 8D and the detection instrument are electrically connected via contacts, the detection instrument selects appropriate technical parameters based on information of different S1 values, finally the detection results are obtained or which kind of instrument model is used or which type of analyte detection is carried out.

Assuming that the ratio of the area of the upper to the lower blocks is 1:2, then $$S1 = K1 * \frac{R1}{R2} = K1 * \frac{2}{1} = 2K1$$

The Sixth Embodiment of the Information Identification Device

Figures 9A, 9B, 9C, 9D, 9E:
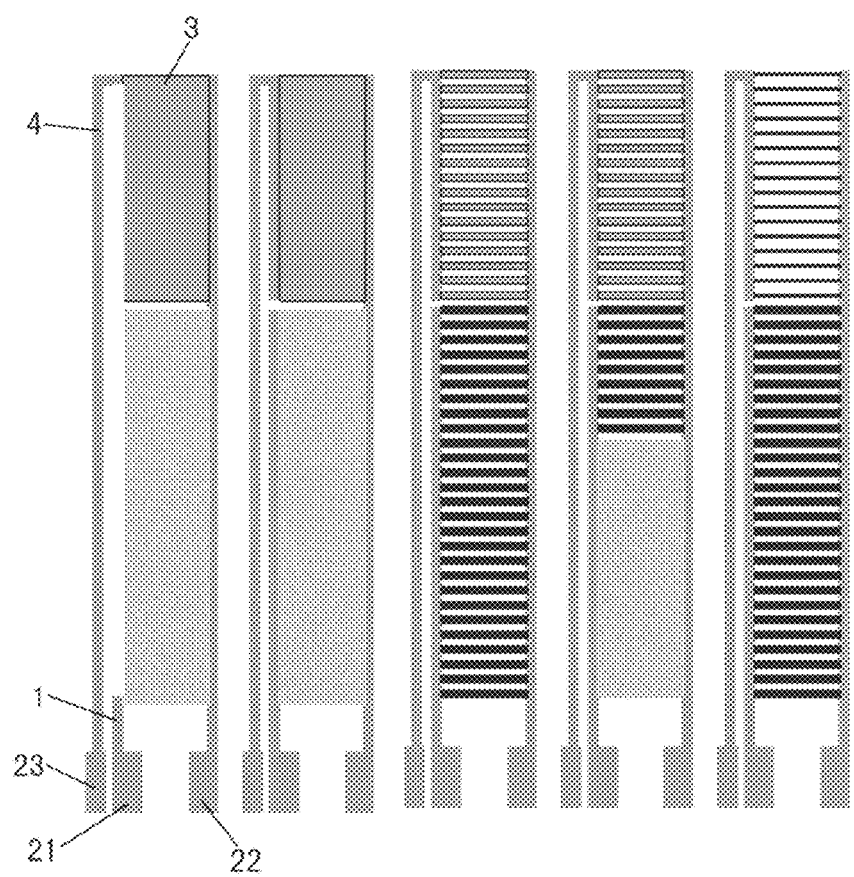
FIG. 9A to FIG. 9E are schematic diagrams of a resistance structure according to an embodiment of the invention.

Referring to FIG. 9A to 9E, taking FIG. 9A as an example, if the ratio of area of the first resistance element 3 at the upper part to the first resistance element 3 at the lower part is 1:2, and the ratio of conductivity is 1:3, then R1:R2=6:1, $$S1 = K1 * \frac{R1}{R2} = K1 * \frac{6}{1} = 6K1$$

For another example, taking FIG. 9D as an example, if the ratio of material conductivity of the upper and the lower two first resistance elements 3 is 1:3, the resistance of single first resistance element 3 at the lower part is n, and the area of the lowest electrode block is 20 times of the area of the first resistance element, then $$S1 = K1 * \frac{R1}{R2} = K1 * \frac{\left(\frac{1}{3n}\right) * x_1}{\left(\frac{1}{n}\right) * x_2 + \left(\frac{\frac{1}{n}}{20}\right)} = K1 * \frac{3(20 + x_2)}{x_1}$$

According to different biosensor production batches, different calibration parameter calibration equations, and instrument models or different analytes to be determined, the electrodes of detection instrument can be connected to different contacts, thereby the information identification device gives different resistance ratio Sn. The detection instrument selects appropriate technical parameters based on different information of Sn and the combinations thereof, finally the detection results are obtained or which type of analyte detection is carried out.

Figure 21:
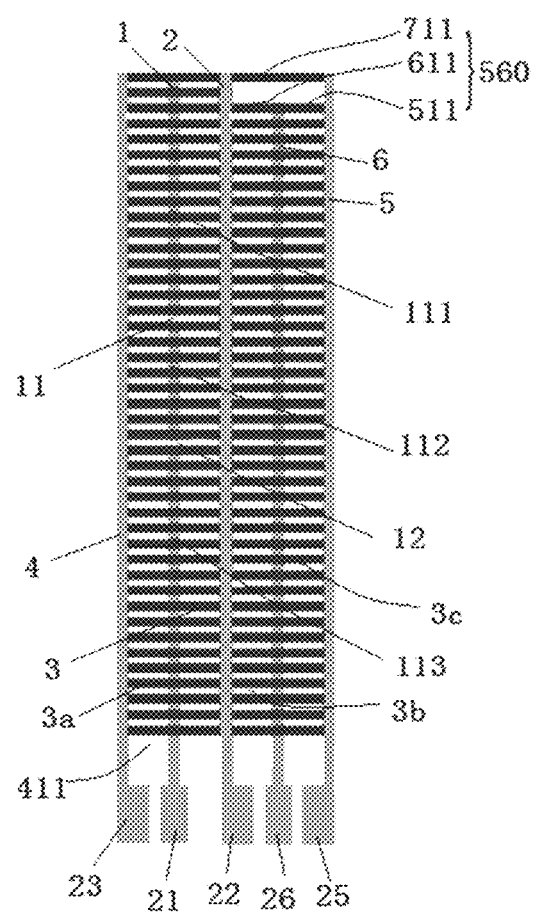
FIG. 21 schematically illustrates a variant of the resistance structure and information identification device according to the present invention.
Figure 22:
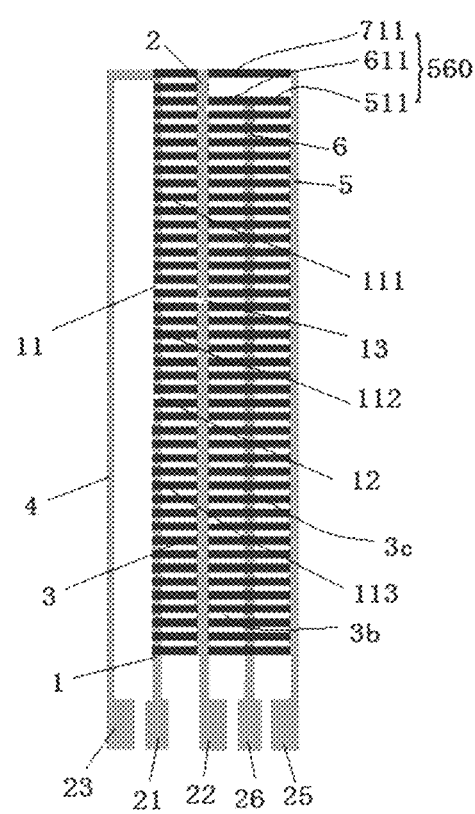
FIG. 22 schematically illustrates a variant of the resistance structure and information identification device according to the present invention.
Figure 23:
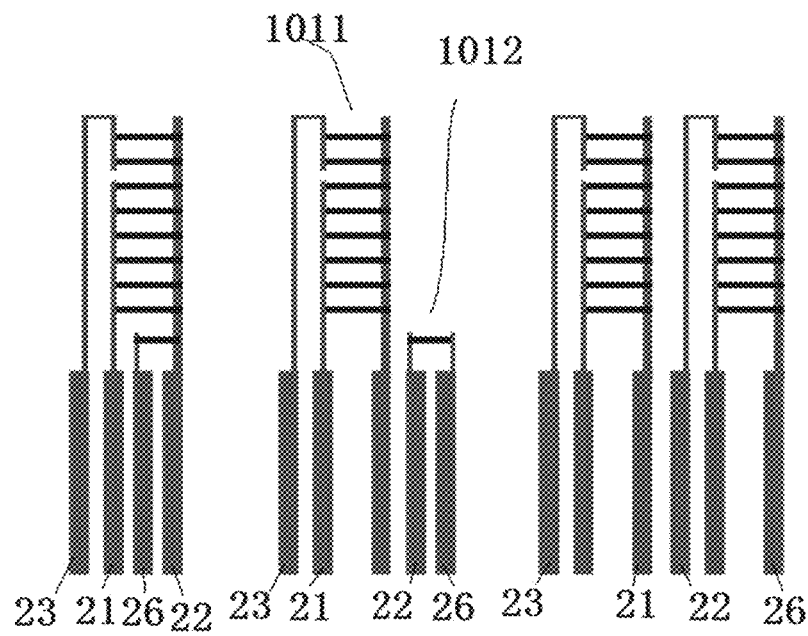
FIG. 23 schematically illustrates a variant of the resistance structure and information identification device according to the present invention.

FIGS. 21-23 show variant forms of resistance structure and information identification device according to the present invention.

As shown in FIG. 23, the information identification device can be obtained by modification and/or combination of the structure shown in FIG. 6.

The structure shown in FIG. 23 may include a plurality of units, such as unit 1011 and unit 1012. Each unit may include an information identification device as shown in FIG. 6 or a portion thereof. For example, the unit 1011 is the structure shown in FIG. 6; and the unit 1012 is a portion of the structure shown in FIG. 6, i.e., the third electrode 4 and contact 23 are removed from the structure shown in FIG. 6. The plurality of units may be electrically connected or electrically isolated, as shown in FIG. 23.

A plurality of units can correspond to a code or part of code according to the formula Sn=Kn*Ra/Rb, where Ra and Rb are different electrical parameters determined by the same unit among multiple units or different electrical parameters determined by the combination of different units, or Ra can be a different electrical parameter determined by one or more units among multiple units while Rb can be another independent electrical parameter. Kn is the coefficient, Sn varies with the position of first fracture, as shown in FIG. 6. The electrical parameters and another independent electrical parameter may include resistance, voltage and current.

Referring to FIGS. 21-22, the first sub-resistance structure 411, including at least one resistor 3a, where the first sub-resistance structure connects the third electrode 4 to at least one of the (N+1) parts of the first electrode 1. The second sub-resistance structure, including at least one resistance element 711 or resistance element 711 and resistance element 511 (resistance structure 511 includes at least one resistance element 3c), to connect fourth electrode 5 to at least part of second electrode 2.

Referring to FIGS. 21-22, the third resistance structure 61 includes at least one resistor 3b, to connect the fifth electrode 6 to at least part of second electrode 2 or one of (N+1) parts 111, 112 and 113.

The first sub-resistance structure 411, the second sub-resistance structure 560, and the third sub-resistance structure 611 can be used to expand the structures of resistance structures and information identification devices, and determine various electrical parameters and electrical parameter ratios through combination of different contacts, as shown in FIGS. 21-23, but not limited thereto.

Referring to FIG. 23, another variant of the resistance structure may include a first resistance structure 1011, a second resistance structure 1012, a first contact 21 connected to the first resistance structure, a fifth contact 25 connected to the second resistance structure, a third contact 23 connected to the first resistance structure, a sixth contact 26 connected to the second resistance structure. The first resistance structure 1011 and the second resistance structure 1012 may be independent resistance structures or may be associated resistance structures.

The first resistance structure 1011 may include: a first electrode 1; a second electrode 2; a plurality of first resistance elements 3, wherein one end of each of the first resistance elements 3 is connected to the first electrode 1, and the other end thereof is connected to the second electrode 2; at least one fractures 11 and 12, dividing the first electrode 1 into at least two parts 111, 112 and 113, at least one of fractures 11 and 12 being located two adjacent first resistance elements 3 or disconnecting at least one first resistance element 3 from the first electrode 1.

A first electrical parameter R1 is provided between the first contact 21 and the third contact 23, and a second electrical parameter R2 is provided between the fifth contact 25 and the sixth contact 26. The resistance structure is configured such that the first electrical parameter R1 varies with the position of at least one of the fractures 11 and 12.

According to some embodiments, the second resistance structure may include at least a portion of the first resistance structure, as shown in FIGS. 21-23.

According to some embodiments, one of the fifth contact 25 and the sixth contact is 26 a common contact common to one of the first contact 21 and the third contact 23, that is, as shown in FIGS. 21-22, the first resistance structure is connected with the second resistance structure, and the first contact 21 can be used as a contact to match with the third contact 23 and the sixth contact 26. In this case, the fifth contact 25 may be omitted.

According to some embodiments, the resistance structure may be configured such that the second electrical parameter R2 varies with the position of at least one of the fractures 11 and 12.

According to some embodiments, the second resistance structure may include: a second electrode 2; a fifth electrode 6; a plurality of second resistance elements 3b each having one end connected to second electrode 2 and the other end connected to fifth electrode 6; At least one of the second electrode 2 and the fifth electrode 6 has at least one second fracture 13 such that the second electrode 2 or/and the fifth electrode 6 is divided into at least two parts, and at least one second fracture 11 and 12 are each located between two adjacent first resistance elements 3 or dividing at least one first resistance elements 3 from the second electrode 2 or the fifth electrode 6.

The second resistance structure may be configured similarly to the first resistance structure. The configuration of the first resistance structure and the second resistance structure is not limited to the illustrated example, which may be any structure disclosed in the invention. The configuration of the second resistance structure may include any resistance element, including but not limited to that shown in FIGS. 21-23.

The information identification device may include the above resistance structure. The first electrical parameter R1 and the second electrical parameters R2 may correspond to a code or a portion of a code according to the formula Sn=Kn*Ra/Rb, where Sn is code or a portion of a code, Ra is one of R1 and R2, Rb is one of R1 and R2, and Kn is a coefficient. According to some embodiments, Kn is associated with a manufacturing process.

In any one of the foregoing structures, the resistance of the plurality of first resistance elements 3 may be the same as each other.

In any one of the foregoing structures, the resistance of at least part of the plurality of first resistance elements 3 may be different from each other.

In any one of the foregoing structures, the materials of the first electrode 1 and the second electrode 2 may be different from those of the first resistance element 3.

In any one of the foregoing structures, both the resistance of the first electrode 1 and that of the second electrode 2 may be less than the resistance of each first resistance element 3.

In any one of the foregoing structures, a first electrode 1 and a second electrode 2 may include silver, and a plurality of first resistance elements 3 may include graphite.

In any one of the foregoing structures, the second electrode 2 further has M third fractures 13, M being a natural number greater than 0, each of the M third fractures 13 being located between two adjacent first resistance elements 3 or disconnecting at least one first resistance element 3 from the second electrode 2.

In any one of the foregoing structures, the materials of the plurality of first resistance elements 3 are the same each other. The material and size may be the same each other.

In any one of the foregoing structures, the plurality of first resistance elements 3 include a plurality of resistor stripes disposed in parallel to each other.

In any one of the foregoing structures, the plurality of first resistance elements 3 include at least two resistor discs.

In any one of the foregoing structures, the material of part of the plurality of first resistance elements 3 may be different from that of other first resistance elements 3.

In any one of the foregoing structures, the size of part of the plurality of first resistance elements 3 is different from that of other first resistance elements 3.

In any one of the foregoing structures, a fracture is formed by laser cutting or mechanical perforating way.

Example of Biosensor

Figure 10:
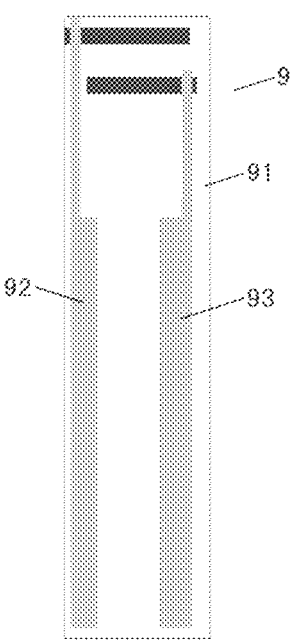
FIG. 10 is a schematic diagram of a biosensor for detecting analytes.

FIG. 10 is a schematic diagram of a biosensor body for detecting analytes. The biosensor body 9 may incorporate the aforesaid information identification device 1 to constitute a biosensor. As shown in FIG. 10, the biosensor body 9 includes a working electrode 92 and a counter electrode 93, and an insulating substrate 93 for disposing two test electrodes. At least one of the working electrode 92 and the counter electrode 93 is provided with a reaction reagent layer.

Figure 11:
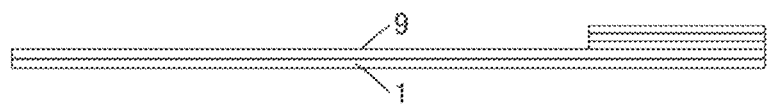
FIG. 11 is a schematic diagram of a biosensor with information identification device according to an embodiment of the invention.

FIG. 11 shows a schematic diagram of a first biosensor with an information identification device according to an embodiment of the present invention. As shown in FIG. 11, the information identification device 1 is disposed on the back surface of the biosensor body 9 and is electrically isolated from the working electrode 92 and a counter electrode 93 through the insulating substrate 93, of which, the uppermost three-layer structures are reaction layer, channel layer and upper cover layer respectively.

Figures 12, 13:
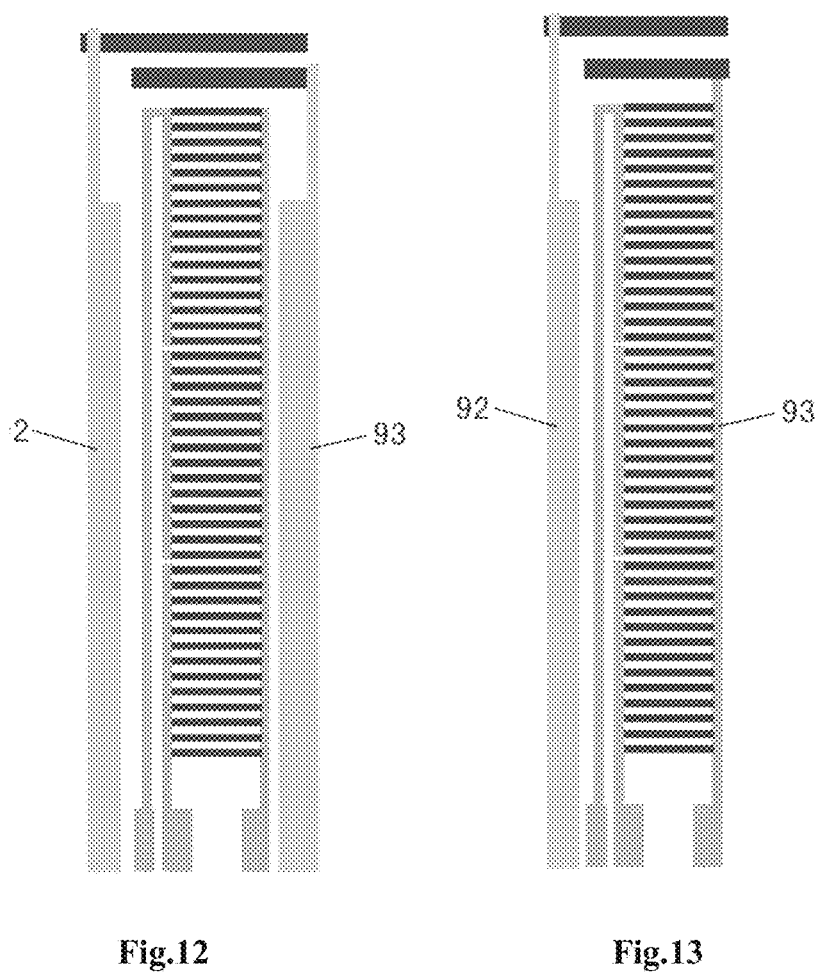
FIG. 12 is a schematic diagram of a biosensor with information identification device according to an embodiment of the invention.
FIG. 13 is a schematic diagram of a biosensor with information identification device according to an embodiment of the invention.

FIG. 12 shows a schematic diagram of a second biosensor with an information identification device according to an embodiment of the present invention, wherein the information identification device 1 is located on the front side of the biosensor body 9 and is isolated from the working electrode 92 and the counter electrode 93.

FIG. 13 shows a schematic diagram of a third biosensor with an information identification device according to an embodiment of the present invention, wherein the information identification device 1 is located on the front side of the biosensor body 9 and is adjacent to the working electrode 92 and the counter electrode 93. Information identification device 1 is connected with the counter electrode 93 of biosensor to save space, while electrical isolation may simplify the instrument design, thus, those skilled in the art may select them as required.

Figure 24:
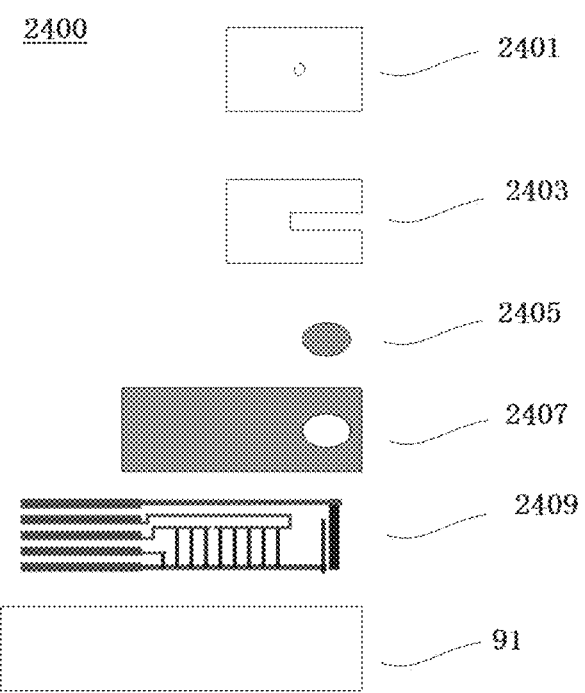
FIG. 24 schematically illustrates an exploded structural view of a biosensor according to some embodiments of the present invention.

FIG. 24 schematically illustrates a structural exploded view of a biosensor according to some example embodiments of the present invention.

Referring to FIG. 24, a biosensor 2400 according to some embodiments of the present invention includes an insulating substrate 91, a functional electrode and an information identification device 2409, an insulating layer 2407, a reaction reagent layer 2405, a channel layer 2403, and a top cover layer 2401.

The insulating substrate 91 may, for example, be an insulating sheet, which is electrically insulative. The materials for the insulating substrate 91 may include, but not limited to, polyethylene terephthalate, polyethylene, polystyrene, polyester, polypropylene, polycarbonate, polyvinyl chloride, resin, ceramics, and other insulating materials.

The function electrode and information identification device 2409 may include a working electrode 92 and a counter electrode 93 and an information identification device as described above. The working electrode 92 and counter electrode 93 are used as functional electrodes. The functional electrodes are not limited to the working electrode and the counter electrode, and other electrodes may be added according to the practical applications.

The information identification device and the functional electrodes may be located on the same surface of the insulating base plate 91. In this case, the information identification device may be electrically isolated from the working electrode 92 and the counter electrode 93 or may be connected to one of the working electrode 92 and the counter electrode 93. Besides, FIG. 24 shows that the information identification device and the functional electrode are located on the same surface of the insulating base plate 91, but the present invention is not limited thereto, for example, the information identification device and functional electrodes may be located on different surfaces of the insulating base plate 91.

The materials used for the functional electrode may be any appropriate conductive material, including but not limited to, carbon, silver or silver chloride, gold, platinum and a mixture with other appropriate conductive material or conductive substance or combinations thereof. For example, the electrode at the end in contact with reaction reagent may use graphite, and the part of the electrode at the rear end in contact with detection instrument may use a silver material.

The information identification device may be any of the information identification devices or variants thereof as described above. The information identification device may include any of the resistance structures or variants thereof as described above. The resistance element of information identification device may be a resistor stripe, or a standard resistor disc.

The insulating layer 2407 includes an opening to expose a portion of the working electrode and the counter electrode. The material of the insulating layer may include, without limitation to, thermal drying type insulating ink or ultraviolet curing type insulating ink, insulating tape, and etc.

The reaction reagent layer 2405 is disposed in the opening of the hydrophobic insulating layer, which contains reagents for identifying biological samples and varies with the test samples. For example, the reaction reagents of an electrochemical biosensor include an oxidoreductase and an electron mediator that react with a sample to generate an electrical signal.

The channel layer 2403 is a channel for sample injection, which functions together with the pore of the top cover layer. Samples enter the channel via the capillary force. During sample injection, the air at the front end of channel is discharged via the pore to achieve smooth sample injection. The material of channel layer includes but not limited to double-sided adhesive tape.

The top cover layer 2401 includes a pore, which is located at the top of the channel of the channel layer away from the inlet end. The lower surface of the top cover layer may be coated with a hydrophilic material. The pore and hydrophilic material may enhance the capillary action of the channels. The material of the top cover layer is transparent or translucent, to facilitate observation of sample injection or not in the reaction zone.

Depending on the identification information carried by the identification information system, the detection system may select the corresponding technical parameters, to finally obtain the test results or judge which type of analyte is to be tested.

The electrical parameters described herein include but not limited to resistance, current, voltage, etc.

Compared with the prior art, the structures and constructions of the information identification device and biosensor disclosed herein can reduce the cost, simplify the processing complexity, and facilitate information expansion.

It should be noted that, the methods for generating correction parameters of the biosensor and the information identification device described herein are not limited to graphical examples listed above, which should include various solutions devised within the concept of the invention.

For example, a resistance structure according to the present disclosure may be used in combination, the resistance structure may include a first electrode; a second electrode; a plurality of first resistance elements, wherein one end of each of the first resistance elements is connected to the first electrode, and the other end thereof is connected to the second electrode; a first fracture, the first fracture dividing the first electrode into a first part and a second part, the first fracture being located between two adjacent first resistance elements or disconnecting at least one first resistance element from the first electrode. It will be readily understood that various information identification devices can be obtained by combining the resistance structures according to the present invention without departing from the spirit and instructions of the present invention. The plurality of information identification devices may have different coding schemes. The above resistance structure can also be applied to other circumstances in addition to embodiments of the present invention.

The aforesaid resistance structure may further include a third electrode, wherein the third electrode is connected to the first part of the first electrode; a first contact, connecting with the second part of the first electrode; a second contact, connecting with the second electrode; and a third contact, connecting with the third electrode.

The second part of the aforesaid first electrode further has N second fractures, N being a natural number greater than 0, each of the N second fractures being located between two adjacent first resistance elements or disconnecting at least one first resistance element from the first electrode, and the N second fractures divide the first part into (N+1) parts.

The aforesaid second electrode (2) further includes M third fractures, M being a natural number greater than 0, each of the M third fractures being located between two adjacent first resistance elements or disconnecting at least one first resistance element from the second electrode, and the M third fractures divide the second electrode into (M+1) parts.

The aforesaid resistance structure may further include a third electrode, a plurality of fifth electrodes, wherein one end of each of the fourth electrode is connected to the second electrode or the first electrode, and the other end thereof is connected to the third electrode. At least one of the second electrode and the third electrode may have a plurality of first fractures, the first fractures being located between two adjacent first resistance elements or fourth electrodes or disconnecting at least one first resistance element or the fourth electrode from the second electrode.

According to some embodiments, the information identification device includes one of the above resistance structures, wherein at least part of the plurality of first resistance elements has a linear shape.

According to some other embodiments, the information identification device includes one of the above resistance structures, wherein at least part of the plurality of first resistance elements has a curved shape such as a sawtooth shape.

According to some other embodiments, the biosensor includes one of the aforesaid information identification devices. The information identification device and the working electrode 92 and the counter electrode 93 are located on the same surface of the insulating base plate 91, and the information identification device is electrically isolated from the working electrode 92 and the counter electrode 93 or connected to one of the working electrode 92 and the counter electrode 93. The information identification device and the working electrode 92 and the counter electrode 93 are located on different surfaces of the insulating base plate 91.

According to some embodiments, a resistance structure unit may be provided. The resistance structure unit may include any one of the aforementioned resistance structures. The resistance structure unit may be used in an information identification device or other devices.

According to some embodiments, an information identification unit may be provided. The information identification unit may include any one of the aforementioned resistance structures. The information identification unit may be used in an information identification device or other devices.

According to some embodiments, the information identification device is used to identify the identification information through the ratio of an electrical parameter characterized by the resistance structure to a second electrical parameter.

According to some embodiments, the second electrical parameters include resistance, voltage, or current.

According to some embodiments, the second electrical parameters are dependent or independent of the resistance structure.

According to some embodiments, the second electrical parameters are from a test instrument.

It is easy to understand that a resistance structure or a resistance structure unit herein is not limited to be used in biosensor, but used in other appropriate systems. The information identification unit or the information identification device described herein are not limited to be used in biosensor, but used in other appropriate systems.

For the method for judging the information identification device described herein, the electrode may be made of a conductive material such as carbon or silver, and may be made on an insulating substrate by screen printing, plating, etc.

The method for making information identification device is described by taking screen printing as an example. The method includes making of a screen mesh with a preset electrode shape, then printing the conductive material on the insulating substrate using the screen mesh to form a corresponding electrode. The fracture can be pre-set in the screen mesh or made by the laser cutting or mechanical perforating method after the formation of electrode system. By taking the information identification device 1 located on the front side of the biosensor body 9 as an example, first the test paper production is completed, and then the test paper testing is carried out. By selecting appropriate technical parameters of this batch and according to the position of fractures, the fractures are made by the laser cutting or mechanical perforating method, thus, the information identification devices of this batch of test papers are produced.

The electrode of the information identification device is made of conductive material. If these electrodes are directly exposed to the environment, substances in the environment will adhere to the electrode, which will change the actual electrical parameters of the electrode, resulting in inaccurate test data. Thus, in the present invention, the electrodes of the information identification device are coated with an insulating layer, which may be a material having poor electrical conductivity such as a self-adhesive, a plastic sheet, or a UV-curable ink, etc.

The biosensor of the information identification device in the present invention can be used to determine alcohol, glucose, uric acid, lactate, cholesterol, bilirubin, hemoglobin, alanine aminotransferase from an analyte sample such as whole blood, urine, saliva, etc.

The present invention has been described with reference to several typical embodiments, but it should be understood that all terminologies user herein are illustrative and exemplary, rather than restrictive. As this invention can be executed in a variety of forms without departing from the spirit or nature of the invention, it should be understood that the embodiments described above are not limited to any of the foregoing details, but it should be construed broadly within the spirit and scope of the invention as defined by the appended claims. Therefore, all variations and modifications made based on the claims or their equivalents shall fall into the scope of protection of the invention.

The invention claimed is:

1. A resistance structure comprises:
   a first electrode;
   a second electrode;
   a plurality of first resistance elements, wherein one end of each of the first resistance elements is connected to the first electrode, and the other end of each of the first resistance elements is connected to the second electrode;
   a first fracture in the first electrode, the first fracture dividing the first electrode into a first part and a second part, wherein the first fracture is located between two adjacent first resistance elements;
   a third electrode, wherein the third electrode is connected to the first part of the first electrode;
   a first contact, connecting with the second part of the first electrode;
   a second contact, connecting with the second electrode; and
   a third contact, connecting with the third electrode.

2. The resistance structure according to claim 1, wherein the second part of the first electrode further has N second fractures, N being a natural number greater than 0, each of the N second fractures being located between two adjacent first resistance elements or disconnecting at least one first resistance element from the first electrode, the N second fractures divide the first part into (N+1) parts, the third electrode is connected with one of the (N+1) parts.

3. The resistance structure according to claim 1, wherein the resistances of the plurality of first resistance elements are the same as each other.

4. The resistance structure according to claim 1, wherein the resistances of at least part of the plurality of first resistance elements are different.

5. The resistance structure according to claim 1, wherein the material of the first electrode and the second electrode is different from that of the first resistance element.

6. The resistance structure according to claim 1, wherein both the resistance of the first electrode and the second electrode is less than that of each first resistance element.

7. The resistance structure according to claim 1, wherein the second electrode further has M third fractures, M being a natural number greater than 0, each of the M third fractures being located between two adjacent first resistance elements or disconnecting at least one first resistance element from the second electrode.

8. The resistance structure according to claim 1, wherein the first electrode and the second electrode include silver, and the plurality of first resistance elements include graphite.

9. The resistance structure according to claim 1, wherein the materials of the plurality of first resistance elements are the same as each other.

10. The resistance structure according to claim 1, wherein the sizes of the plurality of first resistance elements are the same as each other.

11. The resistance structure according to claim 1, wherein the plurality of first resistance elements comprise a plurality of resistor stripes disposed in parallel to each other.

12. The resistance structure according to claim 1, wherein the plurality of first resistance elements comprise at least one resistor discs.

13. The resistance structure according to claim 1, wherein the material of part of the plurality of first resistance elements is different from that of other first resistance elements.

14. The resistance structure according to claim 1, wherein the size of part of the plurality of first resistance elements is different from that of other first resistance elements.

15. The resistance structure according to claim 1, wherein a fracture is formed by laser cutting or mechanical perforating way.

16. A resistance structure comprises:
   a first electrode;
   a second electrode;
   a plurality of first resistance elements, wherein one end of each of the first resistance elements is connected to the first electrode, and the other end of each of the first resistance elements is connected to the second electrode;
   N fractures in the first electrode, the N fractures dividing the first electrode into N+1 parts, wherein each of the N fractures is located between two adjacent first resistance elements; and wherein N is a natural number greater than 0;
   a first contact;
   a second contact; and
   a third contact,
   each of the first contact, the second contact and the third contact is connected to or connected via a resistance structure to one of the N+1 parts, the resistance structure comprises at least one resistance elements.

17. A resistance structure comprises:
   a first electrode;
   a second electrode;
   a plurality of first resistance elements, wherein one end of each of the first resistance elements is connected to the first electrode, and the other end of each of the first elements is connected to the second electrode;
   N fractures in the first electrode, the N fractures dividing the first electrode into N+1 parts, wherein each of the N fractures is located between two adjacent first resistance elements; and wherein N is a natural number greater than 0;
   a third electrode;
   a fourth electrode;
   a first sub-resistance structure, comprising at least one resistor, where the first sub-resistance structure connects the third electrode to at least one of the (N+1) parts of the first electrode;
   a second sub-resistance structure, comprising at least one resistor, where the second sub-resistance structure connects the fourth electrode to at least part of the second electrode;
   a first contact, connecting one of the (N+1) parts of the first electrode;

a second contact, connecting one of the second contact and the fourth electrode; and
a third contact, connecting with the third electrode.

18. A resistance structure comprises:
a first electrode;
a second electrode;
a plurality of first resistance elements, wherein one end of each of the first resistance elements is connected to the first electrode, and the other end of each of the resistance elements is connected to the second electrode;
N fractures in the first electrode, the N fractures dividing the first electrode into N+1 parts, each of the N fractures is located between two adjacent first resistance elements; and wherein N is a natural number greater than 0;
a third electrode;
a fourth electrode;
a first sub-resistance structure, comprising at least one resistor, where the first sub-resistance structure connects the third electrode to at least part of the second electrode or one of the (N+1) parts;
a second sub-resistance structure, comprising at least one resistor, where the second sub-resistance structure connects the fourth electrode to the third electrode or at least part of the second electrode or one of the (N+1) parts;
a first contact, connected to or connected via a third sub-resistance structure to one of the (N+1) parts of the first electrode, the second sub-resistance structure at least comprises a resistance element;
a second contact; and
a third contact,
wherein, each of the second contact and the third contact is connected to one of the second electrode, the third electrode and the fourth electrode.

19. A resistance structure comprises:
a first electrode;
a second electrode;
a plurality of first resistance elements, wherein one end of each of the first resistance elements is connected to the first electrode, and the other end of each of the first resistance elements is connected to the second electrode;
N fractures in the first electrode, the N fractures dividing the first electrode into N+1 parts, wherein each of the N fractures is located between two adjacent first resistance elements; and wherein N is a natural number greater than 0;
a third electrode;
a first sub-resistance structure, comprising at least one resistor, where the first sub-resistance structure connects the third electrode to at least part of the second electrode;
a first contact;
a second contact; and
a third contact,
each of the first contact and the second contact is connected to or connected via a second sub-resistance structure to one of the (N+1) parts, the second sub-resistance structure comprises at least one resistance element, the third contact is connected with the third electrode.

20. A resistance structure comprises:
a first resistance structure;
a second resistance structure;
a first contact, connected to the first resistance structure;
a second contact, connected to the second resistance structure;
a third contact, connected to the first resistance structure;
a fourth contact, connected to the second resistance structure,
wherein the first resistance structure comprises:
a first electrode;
a second electrode;
a plurality of first resistance elements, wherein one end of each of the first resistance elements is connected to the first electrode, and the other end of each of the first resistance elements is connected to the second electrode;
at least one fractures in the first electrode, dividing the first electrode into at least two parts, wherein each of the fractures is located between two adjacent first resistance elements;
wherein, a circuit parameter between the first contact and the third contact is a first electrical parameter R1, and a circuit parameter between the second contact and the fourth contact is a second electrical parameter R2, the first electrical parameter R1 varies with the location of at least one of the fractures.

21. The resistance structure according to claim 20, wherein the second resistance structure comprises at least a portion of the first resistance structure.

22. The resistance structure according to claim 21, wherein one of the second contact and the fourth contact is a common contact common to one of the first contact and the third contact.

23. The resistance structure according to claim 22, wherein the second electrical parameter R2 varies with the location of at least one of the fractures.

24. The resistance structure according to claim 20, wherein the second resistance structure comprising:
a third electrode;
a fourth electrode;
a plurality of second resistance elements, wherein one end of each of the second resistance elements is connected to the third electrode, and the other end thereof is connected to the fourth electrode;
wherein at least one of the third electrode and the fourth electrode has at least one second fracture such that the third electrode or the fourth electrode is divided into at least two parts, at least one of the second fractures is located between two adjacent first resistance elements.

25. A resistance structure unit, comprising the resistance structure as claimed in claim 16.

26. The resistance structure unit according to claim 25, wherein the resistances of the plurality of first resistance elements are the same as each other.

27. The resistance structure unit according to claim 25, wherein the resistances of at least part of the plurality of first resistance elements are different.

28. The resistance structure unit according to claim 25, wherein the material of the first electrode and the second electrode is different from that of the first resistance element.

29. The resistance structure unit according to claim 25, wherein both the resistance of the first electrode and the second electrode is less than that of each first resistance element.

30. The resistance structure unit according to claim 25, wherein the first electrode and the second electrode include silver, and the plurality of first resistance elements include graphite.

31. The resistance structure unit according to claim 25, wherein the second electrode further has M third fractures, M being a natural number greater than 0, each of the M third fractures being located between two adjacent first resistance elements or disconnecting at least one first resistance element from the second electrode.

32. The resistance structure unit according to claim 25, wherein the materials of the plurality of first resistance elements are the same as each other.

33. The resistance structure unit according to claim 25, wherein the plurality of first resistance elements comprise a plurality of resistor stripes disposed in parallel to each other.

34. The resistance structure unit according to claim 25, wherein the plurality of first resistance elements comprise at least one resistor discs.

35. The resistance structure unit according to claim 25, wherein the material of part of the plurality of first resistance elements is different from that of other first resistance elements.

36. The resistance structure unit according to claim 25, wherein the size of part of the plurality of first resistance elements is different from that of other first resistance elements.

37. The resistance structure unit according to claim 25, wherein a fracture is formed by laser cutting or mechanical perforating way.

* * * * *